United States Patent [19]
Kaltenbach

[11] Patent Number: 5,917,606
[45] Date of Patent: *Jun. 29, 1999

[54] PHOTOMETRIC FLOW APPARATUS FOR SMALL SAMPLE VOLUMES AND METHOD OF MAKING SAME

[75] Inventor: Patrick Kaltenbach, Bischweier, Germany

[73] Assignee: Hewlett-Packard Company, Palo Alto, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/709,017

[22] Filed: Sep. 6, 1996

[30] Foreign Application Priority Data

Sep. 6, 1995 [EP] European Pat. Off. ............... 95113947

[51] Int. Cl.[6] .............................. G01N 21/00; G01N 1/10
[52] U.S. Cl. ............................................ 356/440; 356/246
[58] Field of Search .................................. 356/410, 440, 356/246

[56] References Cited

U.S. PATENT DOCUMENTS

| | | | |
|---|---|---|---|
| 3,751,173 | 8/1973 | Sanz et al. ............................... | 356/246 |
| 4,575,424 | 3/1986 | Allington et al. ....................... | 356/246 |
| 5,061,361 | 10/1991 | Gordon ............................... | 204/299 R |
| 5,141,548 | 8/1992 | Chervet ....................................... | 65/108 |
| 5,171,995 | 12/1992 | Gast et al. .......................... | 356/244 X |
| 5,273,633 | 12/1993 | Wang ................................. | 356/246 X |
| 5,493,405 | 2/1996 | Hulme ................................ | 356/246 X |

FOREIGN PATENT DOCUMENTS

| | | |
|---|---|---|
| 0 266 769 | 11/1987 | European Pat. Off. . |
| 0 396 163 | 2/1990 | European Pat. Off. . |
| 0 488 947 A1 | 11/1991 | European Pat. Off. . |
| 0 523 680 A2 | 7/1992 | European Pat. Off. . |

OTHER PUBLICATIONS

Ahmad A. Abbas, et al., "Optical properties of axial–illumination flow cells for simultaneous absorbance–fluorescence detection in micro liquid chromatography," *Journal of Chromatography*, vol. 691, pp. 37–53.

James W. Jorgenson, et al., "High–resolution separations based on electrophoresis and electroosmosis," *Journal of Chromatography*, vol. 218, pp. 209–216.

James W. Jorgenson, et al., "Zone Electrophoresis in Open Tubular Glass Capillaries," *Analytical Chemistry*, Jul. 1981, pp. 1298–1302.

Xiaobing XI, et al., "Axial–Beam On–Column Absorption Detection for Open Tubular Capillary Liquid Chromatography," *Analytical Chemistry*, Aug. 1, 1990, pp. 1580–1585.

*Primary Examiner*—Robert Kim
*Assistant Examiner*—Amanda Merlino

[57] ABSTRACT

A photometric apparatus (100) for small sample volumes comprises a cell body (102), a light input means (104) arranged adjacent to a first surface of the cell body (102), a light source (105) emitting light of predetermined wavelength or wavelength range through the light input means (104), a light output means (106) arranged adjacent to a second surface of the cell body (102) opposite to the first surface, a light detector (107) arranged adjacent to the light out put means (104), and a flow channel (108) formed in the cell body (102), wherein surfaces of the walls of the channel (108) have a roughness smaller than the predetermined wavelength.

24 Claims, 11 Drawing Sheets

DIFFUSE REFLECTION

SPECULAR REFLECTION

PHOTOMETRIC FLOW APPARATUS FOR SMALL SAMPLE VOLUMES AND METHOD OF MAKING SAME

FIELD OF THE INVENTION

The present invention relates to spectroscopy, and more particularly to spectroscopy of small samples in solution.

BACKGROUND OF THE INVENTION

In sample analysis instrumentation, and especially in separation systems such as liquid chromatography and capillary electrophoresis systems, smaller dimensions generally result in improved performance characteristics and at the same time result in reduced analysis costs. These techniques are preferably performed using capillaries having small inside diameters ranging from 5 to 100 micrometers for handling the extremely small volumes of flowing liquid samples.

As an example, the micro-column liquid chromatography ($\mu$LC) has been described wherein columns having diameters of 100–200 $\mu$m are employed as compared to columns having diameters of around 4.6 mm.

Another approach has been the use to capillary electrophoresis, a separation technique carried out in capillaries having a diameter of 5–100 $\mu$m.

The capillary electrophoresis has been demonstrated to be useful as a method for the separation of small solutes. See for example Journal of Chromatography, vol. 218, p. 209, 1981; and Analytical Chemistry, vol. 53, p. 1298, 1981.

However, there remain several major problems inherent to those technologies.

For instance, there exist substantial detection limitations in conventional capillary electrophoresis technology. For example in the case of the capillary electrophoresis, optical detection is generally performed on-column by a single-pass detection technique wherein electromagnetic energy, in the form of a light beam is passed through the sample, the light beam travels normal to the capillary axis and crosses the capillary only once. Accordingly, in conventional capillary electrophoresis systems, the detection path length is inherently limited by the diameter of the capillary.

According to Beer's law, absorbance is related to pathlength by the following equation:

$$A = e \ast b \ast C$$

where:
  A = the absorbance
  e = the molar absorptivity, (l/m*cm)
  b = pathlength (cm)
  c = concentration (m/l)

From the above equation it is readily understood that the absorbance (A) of a sample in a 25 $\mu$m capillary is 400 times lower than to the absorbance of a conventional cell having a pathlength of 1 cm, as typically used in ultraviolet, visible (UV/Vis) spectroscopy.

Standard detection cells used in conventional liquid chromatography instruments have the disadvantage that their cell volume is about of three orders of magnitude too large to handle the small nano-liter (nl) sample volumes of the above mentioned capillary separation techniques. Scaling down the conventional shape of these cells to match the nl volumes is problematic both from the manufacturing point of view and from the photometric aspect. For example, to get a cell volume of approximately 10 nl with a pathlength of 1 mm, the circular inner diameter of such a cell has to be smaller than 120 $\mu$m.

With standard UV and UV/Vis detection approaches using conventional lamps such as deuterium lamps or Xenon flash-lamps, it is difficult to pass enough light through such a narrow channel. The loss in light throughput counteracts any gain in optical pathlength, and a sensitivity enhancement over on column detection is no longer possible.

Furthermore, with the state of the art machining tools, e.g., drilling, milling or ultrasonic machining tools it is very difficult to scale down the size of these detection cells to meet these requirements of providing cell volumes in the preferred range of 3–15 nl. Thus, most of the presently available instruments use the above mentioned on column detection approach.

In light of this significant detection limitation, there have been a number of attempts employed in the prior art to extend detection pathlengths, and hence the sensitivity of the analysis in capillary electrophoresis systems.

U.S. Pat. No. 5,061,361 describes an approach entailing micro-manipulation of the capillary flow cell to form a bubble at the point of detection.

U.S. Pat. No. 5,141,548 describes the use of a capillary having a Z-shaped configuration with detection performed across the extended portion of the Z.

Yet another approach has sought to increase the detection pathlength by detecting along the major axis of the capillary (axial-beam detection). See Xi et al., Analytical Chemistry, vol. 62, p. 1580, 1990.

U.S. Pat. No. 5,273,633 describes a further approach to increased detection pathlengths in the field of capillary electrophoresis where a reflecting surface exterior of the capillary is provided. The system also includes an incident window and an exit window downstream of the incident window. Light entering the incident window passes through a section of the capillary by multiple internal reflections before passing through the exit window where it is detected. The multiple internal reflections yield an effective increase in pathlength.

In all of these approaches parts of the light beam do not propagate through the center of the capillary. In all of these approaches at least part of the beam propagates through the transparent capillary wall, and does not contact with the sample. This decreases the linearity of the detector and reduces the effective path length, which determines the sensitivity of the detector.

The European patent application No. 92112114.1 describes a photometric apparatus, having a flow cell coated with a fluoropolymer to guide the light beam axially along a liquid filled tube or capillary. In order to get total internal reflection of the light beam at the cell wall, the fluoropolymer must have a refractive index lower the refractive index of the liquid in the tube. Although these polymers are available, they are very expensive and the stability of the coating when exposed to solvents and acids limits its usability.

While each of the aforementioned approaches has addressed the issue of extending the pathlength, each approach is limited because it entails engineering the capillary after-the-fact or otherwise use difficult technical approaches.

On column detection approaches often use setups similar to those shown in FIG. 8 and FIG. 9.

As shown in FIG. 8 and FIG. 9, in a small area near the outlet a capillary is illuminated with light from a UV/vis light source and a slit of width o is placed behind the capillary to block stray light through the capillary wall. The light transmitted through the slit is detected. Using the Lambert-Beer law, the detector signal for an ideal cell is determined by:

$$A(\lambda) = \epsilon(\lambda) \cdot C \cdot D = \log\frac{I_0(\lambda)}{I(\lambda)}$$

where:
- $A(\lambda)$=absorbance in absorbance units (AU) as a function of the wavelength,
- $\epsilon(\lambda)$=extinction of molar absorption coefficient as a function of the wavelength,
- C=molar solute concentration,
- D=pathlength,
- $I_O$=incident photon flux,
- I=transmitted photon flux.

If stray light through the column wall reaches the detector, the above equation is rewritten as:

$$A = \log\frac{I_0 + I_S}{I + I_S}$$

where:
- $I_S$=stray light through the capillary wall.

FIG. 10 is a typical plot of detector response, plotted as absorbance ($A(\lambda)$) vs. molar solute concentration (C). The lower detection limit is determined by the baseline noise of the detector and its sensitivity, as determined by the slope dA/dc of the detector response linear range absorbance values in the FIG. 10 plot.

The upper limit of detection is determined by the where the detector response is no longer linear, as occurs at higher concentration levels.

Unwanted stray light causes a deviation from the theoretical linear slope according to the Lambert-Beer law. The steepness of the slope compared to typical HPLC detection cells (HPLC=High Pressure Liquid Chromatography) depends on the effective path length (related to the inside diameter of the capillary) and the stray light through the capillary wall. As a result, there is a linear range in which the detector can be operated to get reliable results.

FIG. 11 is a cross sectional view of a prior art flow cell used in liquid chromatography.

The cell assembly 1100 is positioned between a radiation source 1102 and a photodetector device 1104. A lens 1106 is arranged between the radiation light source 1102 and the cell assembly 1100 for focusing the radiation emitted from the radiation source 1102.

A cell body 1108 include a machined conduit 1110 for holding a liquid sample. Windows or lenses 1112 and 1114 are sealed to the cell body 1108 by gaskets 1116. Screws 1118 and 1120 press the windows 1112, 1114 against the cell body 1108.

An inlet tube 1122 and an outlet tube 1124 are connected by threaded fittings 1126 to an inlet port 1128 and an outlet port 1130, respectively, to supply the sample to and from the cell 1100. The tubes 1122, 1124 normally made of stainless steel are connected by threaded fittings 1126 to the cell body 1108.

Typically, these cells 1100 have cell volumes 1110 in the range of 3 to 15 µl. The cell 1100 has an inner diameter of 0.5 to 1.5 mm and a length of 3 to 10 mm. Because the inner diameter of the cell 1100 is such that light rays are prevented from striking the cell wall, there are unpredictable disturbances of the measured photometric signal. Apertures, conical cell shapes and/or lenses are also used to avoid this problem.

Most commonly, deuterium lamps are used as radiation source 1102 for UV/Vis absorbance measurements.

In capillary electrophoresis and µ-liquid chromatography, the sample volumes are about three orders of magnitude smaller than described above. Accordingly, such a flow cell must be much smaller.

Scaling down prior art flow cells of the type described above does not work, since machining operations, e.g. drilling or ultrasonic machining, are not suitable for such small dimensions.

Furthermore, the light throughput through such a small cell is dramatically reduced if no additional changes are made.

Reduced light throughput results in increased photometric noise, to prevent the desired gain in sensitivity from being achieved.

SUMMARY OF THE INVENTION

It is a primary object of this invention to provide a photometric flow cell used for liquid phase detection techniques with small sample volumes, the flow cell having increased detection sensitivity and linearity.

The present invention provides a photometric apparatus for small sample volumes comprising a cell body; a light input means arranged adjacent a first surface of the cell body; a light source emitting light of predetermined wavelength or wavelength range through the light input means; a light output means arranged adjacent a second surface of the cell body opposite to the first surface; a light detector arranged adjacent to the light output means; and a flow channel formed in the cell body; wherein surfaces of the walls of the channel have a roughness smaller than the predetermined wavelength, i.e. of the source.

The cell body is preferably made of non-transparent material, so that light from the light source passes through the channel, but not through the cell wall.

Maximum linearity is accomplished by avoiding stray light through the channel wall.

The connected capillaries preferably have an expanded inner diameter at the outlet to reduce liquid flow disturbances and to match the inner diameter of the capillary to the channel diameter. Dead volumes are avoided by butt coupling the capillary to the channel.

This combination allows highly sensitive and linear detection of nl liquid sample volumes while maintaining the efficiency of capillary separation techniques.

DETAILED DESCRIPTION OF THE PREFERRED EMBODIMENTS

Before the invention is described in detail, it is to be understood that this invention is not limited to the particular component parts of the devices described as such devices may vary.

It is also to be understood that the terminology used herein is for purposes of describing particular embodiments only, and is not intended to be limiting.

It is also to be understood that the same basic construction can not only be used for absorbance measurements, but also for fluorescence or Raman spectroscopy or colorimetry, with flowing or static samples.

In this specification and in the claims which follow, reference will be made to a number of terms which shall be defined to have the following meanings:

The term "liquid phase analysis" is used to refer to any analysis which is done on either small and/or macromolecular solutes in the liquid phase.

The term "liquid phase analysis" as used herein includes chromatographic separations, electrophoretic separations, and electrochromatographic separations.

The term "chromatographic process" generally refers to preferential separations of components, and includes reverse-phase, hydrophobic interaction, ion exchange, molecular sieve chromatography and like methods.

The term "electrophoretic separation" refers to the migration of particles or macromolecules having a net electric charge where the migration is influenced by an electric field. Therefore "electrophoretic separation" includes separations performed in columns packed with gels (such as polyacrylamide, agarose and combinations thereof) as well as separations performed in solution.

The term "electrochromatographic separation" refers to combinations of electrophoretic and chromatographic techniques.

In the following a preferred embodiment of the present invention is described.

A flow cell according to the preferred embodiment is used for analysing small liquid sample volumes, i.e. volumes as small as 3–15 nl.

This is accomplished by a design that allows a high light flux through the cell, and features minimize flow disturbances to maintain high efficient separations.

Figure 1A:
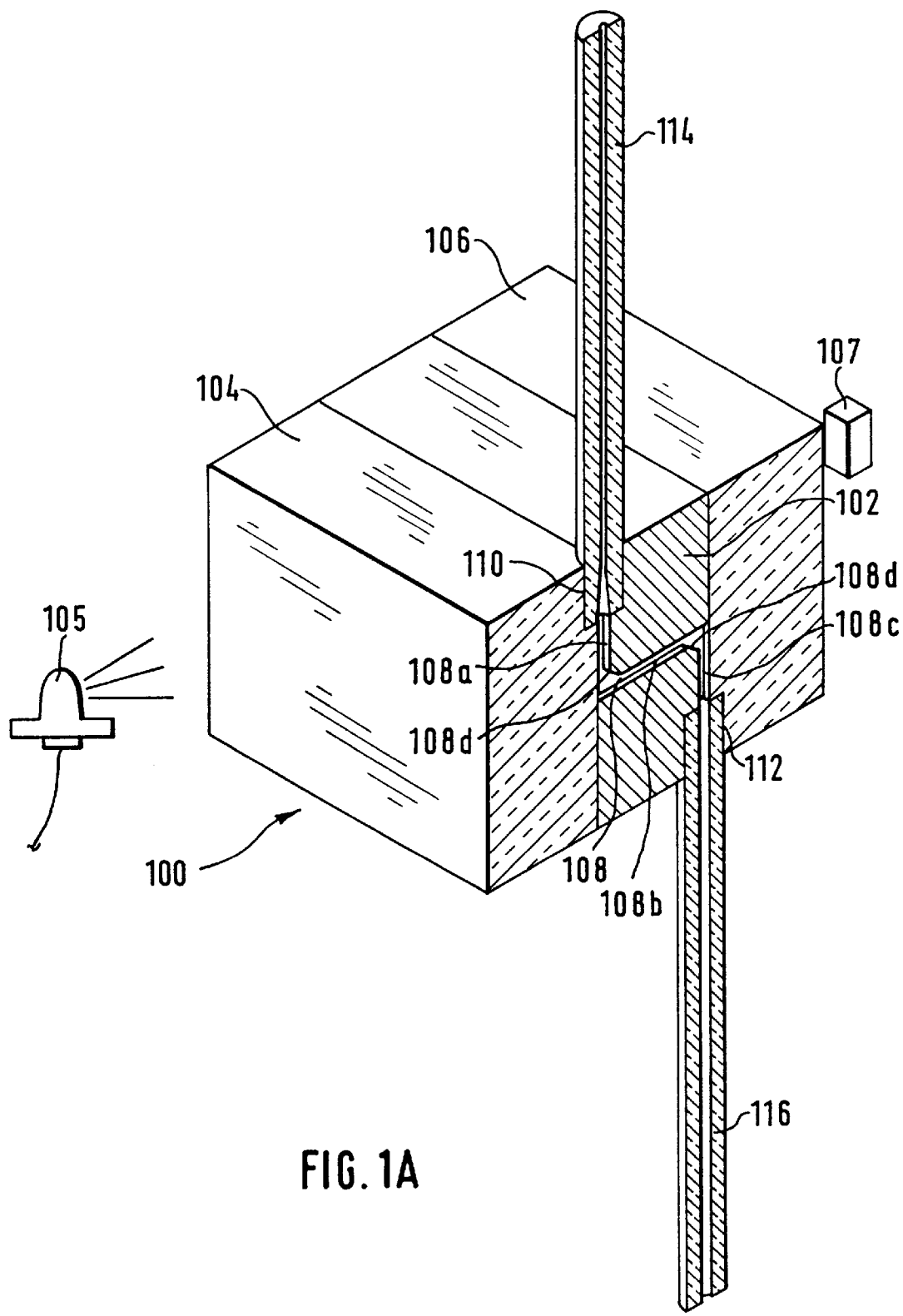
FIG. 1A is a cross-sectional view of a first embodiment of the present invention.

FIG. 1A is a cross sectional view of a photometric flow apparatus 100 according to an embodiment of the present invention.

The photometric flow cell 100 comprises a cell body 102 of a non-transparent material. A first transparent window 104 is arranged adjacent to a first surface of the cell body 102.

A light source 105 and/or light guiding means (not shown) such as lenses or mirrors, is arranged adjacent to the first transparent window 104 for emitting light of a predetermined wavelength or wavelength range therethrough.

A second transparent window 106 is arranged adjacent to a second surface of the cell body 102 opposite to the first surface.

A photo detector means 107 is arranged adjacent to the second transparent window 106. The photodetector means 107 can include mirrors, gratings (not shown) and photo diode arrays.

A flow channel 108 is formed inside the cell body 102. According to the embodiment shown in FIG. 1A the flow channel 108 comprises three portions 108a, 108b, 108c. The first portion 108a of the flow channel 108 is formed adjacent to the first transparent window 104 and extends substantially parallel to the first surface of the cell body 102. The second portion 108b of the flow channel 108 extends from the first surface to the second surface of the cell body 102. The third portion 108c of the flow channel 108 is formed adjacent to the second transparent window 106 and extends substantially parallel to the second surface of the cell body 102.

As can be seen from FIG. 1A the first, second and -third portion 108a–c of the flow channel 108 include junction portions 108d. These junction portions 108d connect the respective portions 108a, 108b and 108b, 108c of the flow channel 108 preferably through an angle of 45°.

It is apparent that angles other than 45° are possible for connection of the flow channel portions.

It is however possible to connect the respective junction portions 108d without any chamfer.

The transparent windows 104, 106 can be made of fused silica and may be directly fused to the cell body 102.

Holes 110 and 112 are provided in the cell 100 for accommodating the ends of an inlet capillary 114 and an outlet capillary 116. These holes 110 and 112 are preferably ultrasonically machined.

In FIG. 1A, a feature concerning the capillary/flow channel coupling in the present invention is shown.

Especially in capillary electrophoresis, it is important to minimize distortions of the electrical field at capillary/flow channel junction portions in order to maintain separation efficiency.

As shown in FIG. 1A, the inlet capillary 114 having a smaller ID (ID=Inner Diameter) than the width of the channel 108 in the cell body 102 is coupled to the cell 100. The inlet capillary 114 has a wider ID at the capillary/flow channel junction to match the diameter to the channel width.

There are different approaches possible to widen the ID of the capillary 114.

In one embodiment, the volume within the capillary is pressurized and the capillary is rotated in a gas flame until the ID of the capillary is increased to the desired extension. This might take a few seconds.

After that, the capillary is scored at the center of the cavity and an axial tension is applied. The capillary will break at the center of the cavity with a clear and rectangular edge. Thus a capillary/flow channel junction is provided having gradual curves and transitions to achieve smooth flow and avoid turbulences.

The capillaries used for microcolumn separations such as capillary electrophoresis or µ-liquid chromatography have inner diameters typically ranging from 25 to 100 µm.

The cell shown in FIG. 1A is designed for very small sample volumes. In this embodiment the flow channel of the cell has a rectangular cross-section of less than 150×150 µm and a channel length of less than 1.3 mm, resulting in a cell volume of less than 10 nl. A detection pathlenght of 1 mm results in a sensitivity up to 20 times higher than on column detection approaches using 50 μm-ID fused silica capillaries.

In one preferred embodiment, the cell body 102 is made of a non-transparent material, such as opaque black Suprasil (registered trademark) (black fused silica) available from Heraeus.

Figure 1B:
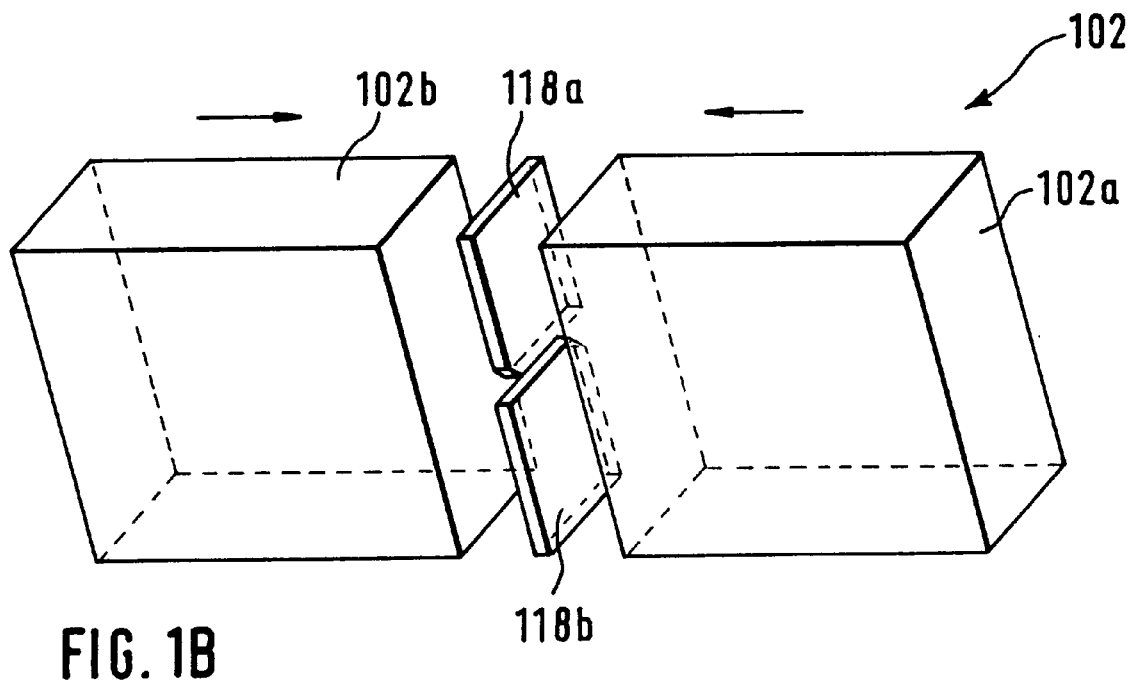
FIGS. 1B and 1C are illustrations of the manufacturing process for the cell body.

As shown in FIG. 1B the cell body 102 comprises a first and a second portion 102a and 102b. A first and a second flow channel forming part 118a and 118b are arranged between the first portion 102a and the second portion 102b of the cell body 102 such that the flow channel 108 shown in FIG. 1A is formed. The cell body 102 is formed by directly fusing together the first portion 102a of the cell body 102, the first and second flow channel forming parts 118a, 118b, and the second portion 102b of the cell body.

Such a process is known in the art and often used for cuvettes and the like.

Figure 1C:
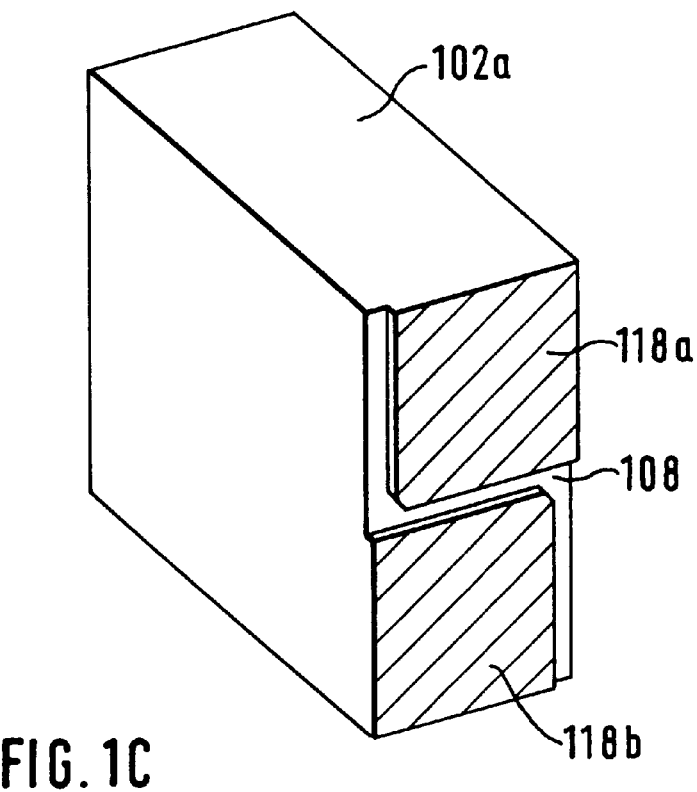

FIG. 1C is a cross sectional view of the cell body 102, showing the flow channel forming parts 118a and 118b and the resulting flow channel 108 in more detail.

The provision of a cell body 102 being non-transparent has a significant advantage in that the occurrence of stray light through the cell wall is prevented.

As already outlined above, this stray light is a known inherent problem in prior art detectors using on column detection or cells with transparent walls. It reduces the linearity of detector and also reduces the effective pathlength and thus the sensitivity.

In a non-transparent cell body the cell output defines a clear aperture which is advantageous if the cell is used for example in a diode array detector.

Before the parts shown in FIGS. 1B and 1C are fused together, the parts are machined and polished to get an even and flat surface. A surface roughness in the order of less than 0.5 μm is to be achieved as this is a requirement for a successive fusing process.

The provision of a superior surface quality is however also a requirement for another essential feature of the present invention. The superior surface quality causes light rays entering the cell and striking the cell wall to be reflected at the same angle as they are incident on this wall.

Figure 2A:
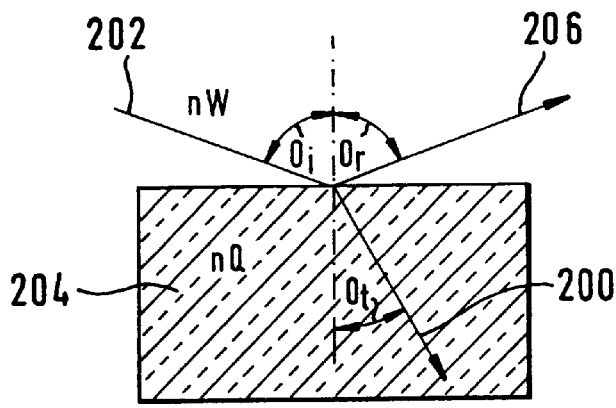
FIG. 2A is a ray diagram of refraction and reflection processes of a light ray incident on a surface of a transparent body.
Figure 2B:
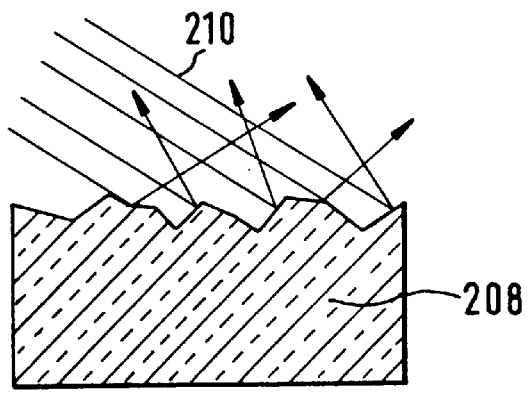
FIGS. 2B and 2C are ray diagrams of the difference between specular and diffuse reflection at the cell wall.
Figure 2C:
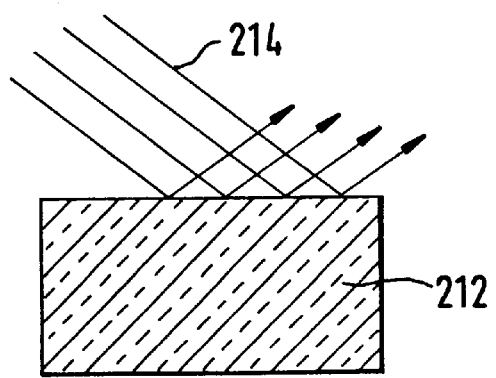

This feature is illustrated in more detail in FIGS. 2A, 2B and 2C.

As shown in FIG. 2A, a first part 200 of an incident light ray 202 on a transmitting medium 204, such as quartz, is refracted into the material 204, while a second part 206 of the incident light 202 is reflected.

While the refraction angle $\Theta_t$ depends on the refractive index n of the media through which the incident and refracted rays propagate, such as air and quartz, the reflection angle $\Theta_r$ always equals the angle of incidence $\Theta_i$.

The amount of light reflected depends on the incident angle $\Theta_i$.

FIGS. 2B and 2C are respectively drawings of ray paths occurring for diffuse and the specular reflection.

As can be seen from FIG. 2B, the surface of a medium 208 has irregularities, wherein these irregularities are large when compared to the wavelength of the incident light 210. These irregularities lead to a diffuse reflection of the incident light 210.

From FIG. 2C medium 212 has a smooth surface having irregularities that are small compared to the wavelength of the reflected light. This is prerequisite for specular reflection of the incident light 214.

Figure 3:
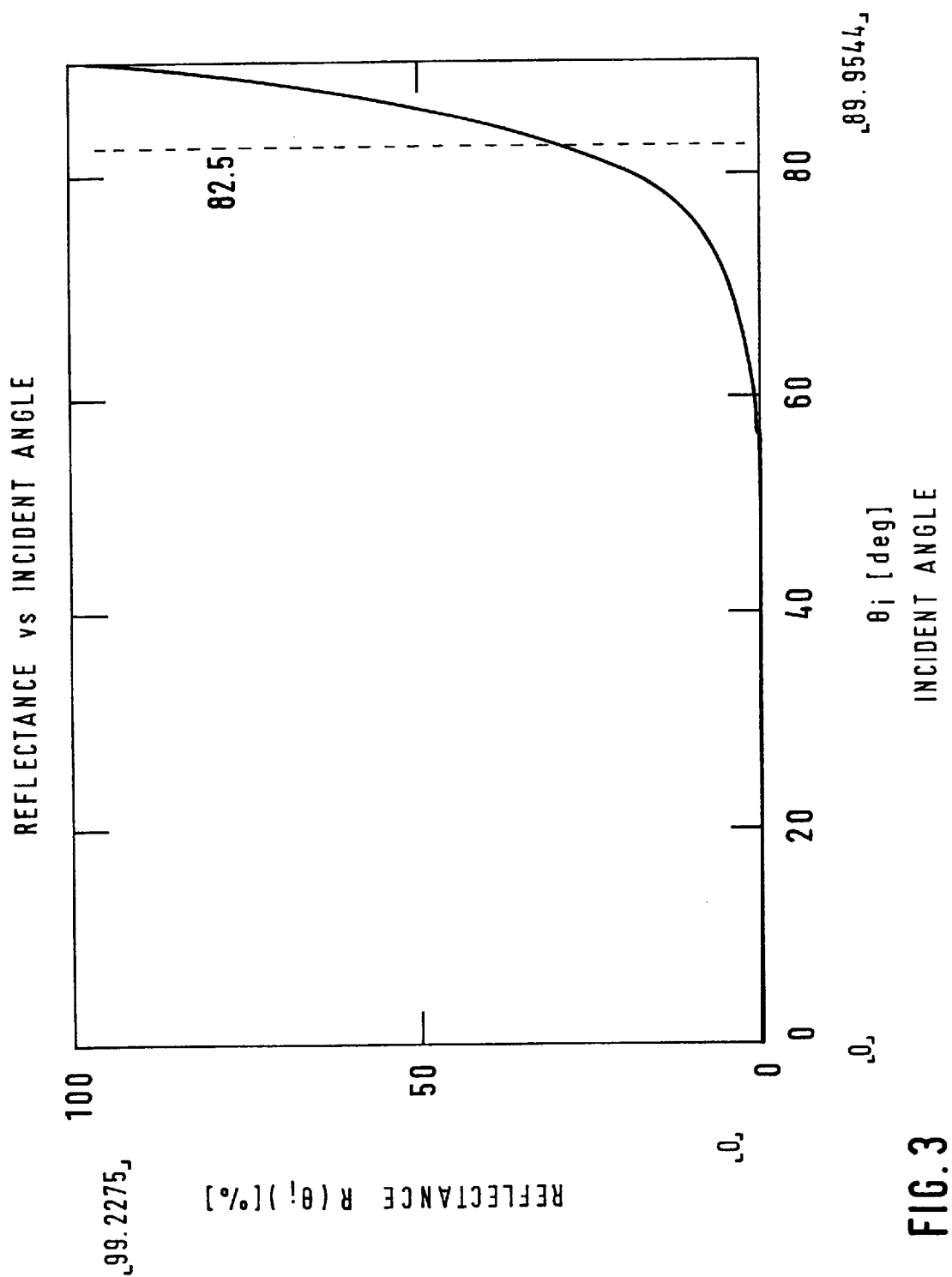
FIG. 3 is a graph of reflectance versus incident angle at a surface of a transparent body.

FIG. 3 is a graph of the reflectance versus incident angle, assuming water (n=1.33) as incident media and quartz (n=1.5) as material into which the light is refracted.

From the graph the amount of reflected light increases dramatically at incident angles higher than 80 degrees and is almost zero for angles less than 60 degrees.

The dependency of the reflectance from the incident angle can be expressed by the following equations:

$$Rp(i) = \frac{(\tan(\theta i - \theta t(i)))^2}{(\tan(\theta i + \theta t(i)))^2}$$

$$Rr(i) = \frac{(\sin(\theta i - \theta t(i)))^2}{(\sin(\theta i + \theta t(i)))^2}$$

$$R(i) = \frac{Rp(i) + Rr(i)}{2}$$

The present invention makes use of this effect to achieve a high light throughput through the cell, to thus keep the photometric noise low. The channel walls are kept even and polished to achieve specular reflection, thus guiding the light through the cell. For UV/Vis detection using conventional light sources, the illumination of small volumes requires fast optics. Since the channel dimensions are small and the channel is narrow, it is important to guide light that enters the cell towards the detector and not to loose it by diffuse reflection at the cell wall.

Figure 4:
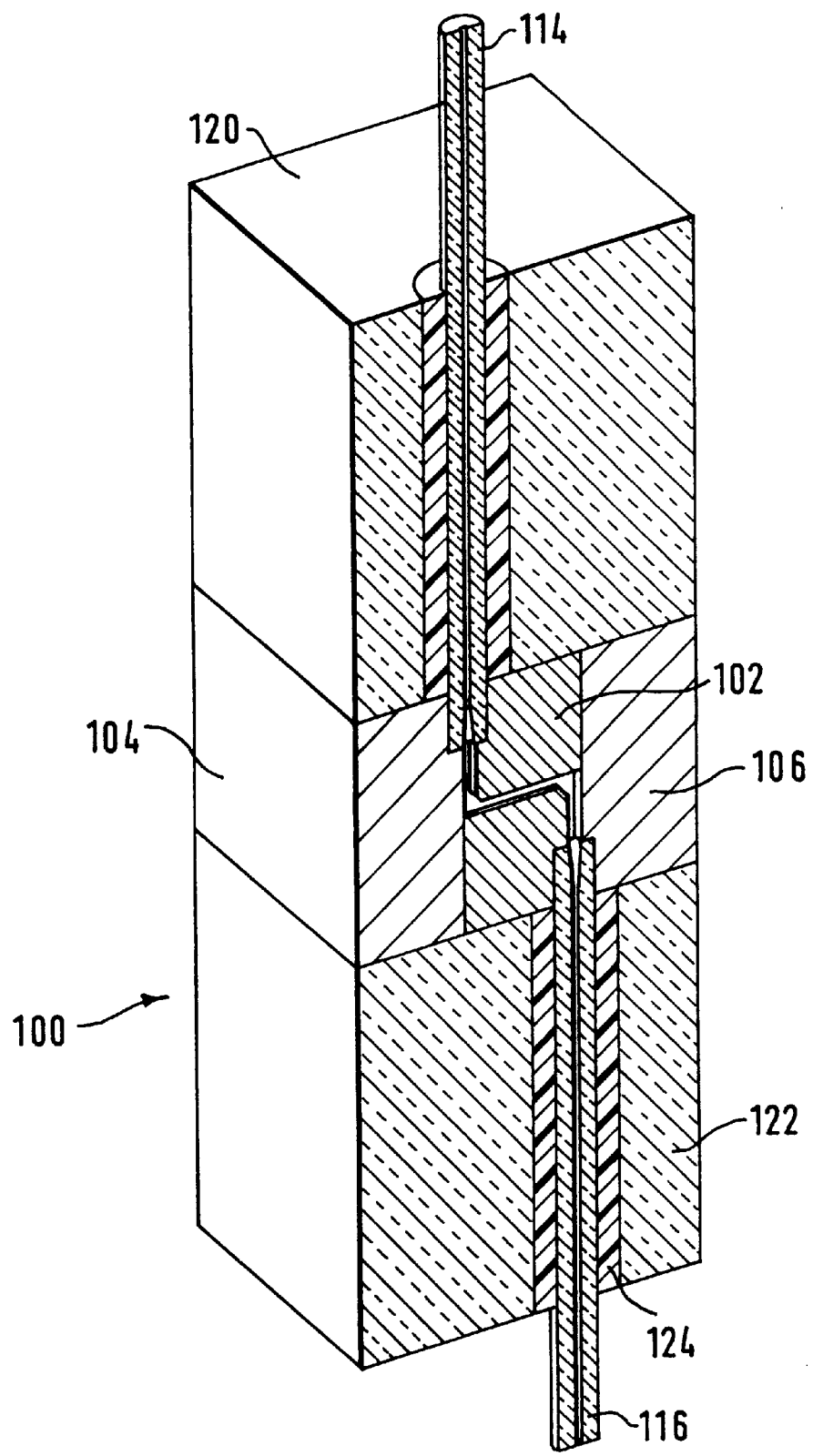
FIG. 4 is a cross-sectional view of a second embodiment of the present invention.

According to a second embodiment shown in FIG. 4, the photometric flow cell 100 further comprises a first capillary support means 120 supporting the inlet capillary 114 and a second capillary support means 122 supporting the outlet capillary 116.

The capillaries 114, 116 can be fixed to the cell using a glue 124, or a plastic fittings which are commonly employed to seal the capillary to the cell.

It is apparent that other means for guiding and attaching the capillaries can be used.

Figure 5:
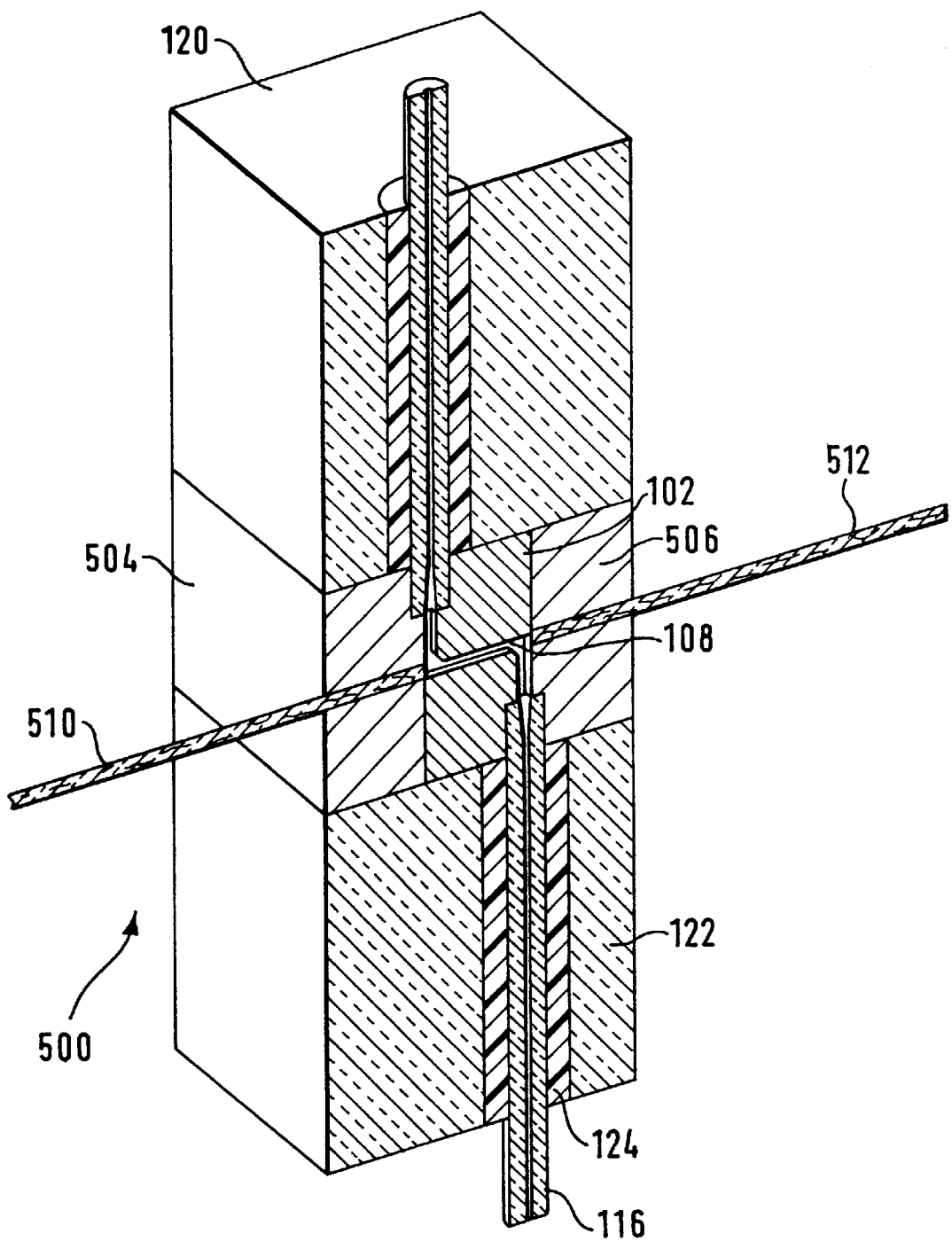
FIG. 5 is a cross-sectional view of a third embodiment of the present invention.

FIG. 5 is a drawing of a third embodiment of the present invention. The flow cell 500 shown in FIG. 5 corresponds partially to the first and second embodiment, so that the description of similar parts having the same reference signs as in the first and second embodiment is omitted.

Contrary to the first and second embodiments the flow cell 500 shown in FIG. 5 does not comprise a first and a second transparent window.

The flow cell 500 comprises a first non-transparent portion 504 arranged adjacent to the first surface of the cell body 102 and a second non-transparent portion 506 arranged adjacent to the second surface of the cell body 102.

According to the third embodiment the light is guided from a light source (not shown) to the cell body 102 by an optical input waveguide 510.

Preferably the light guided to the flow cell 102 by the input waveguide 510 travelling through the channel 108 is collected by an optical output fibre 512 which guides the light to any kind of optical detector such as a photomultilier, a diode, a spectrometer, etc.

Preferably the non-transparent portions 504, 506 are formed by Black Suprasil (registered trademark).

It is to be noted that the fibres 510, 512 are preferably in direct communication with the flow channel 108.

The embodiment shown in FIG. 5 is advantageous in that it allows remote measurement and/or a thermal isolation of the liquid guiding means in a liquid phase analysis instrument.

Figure 6:
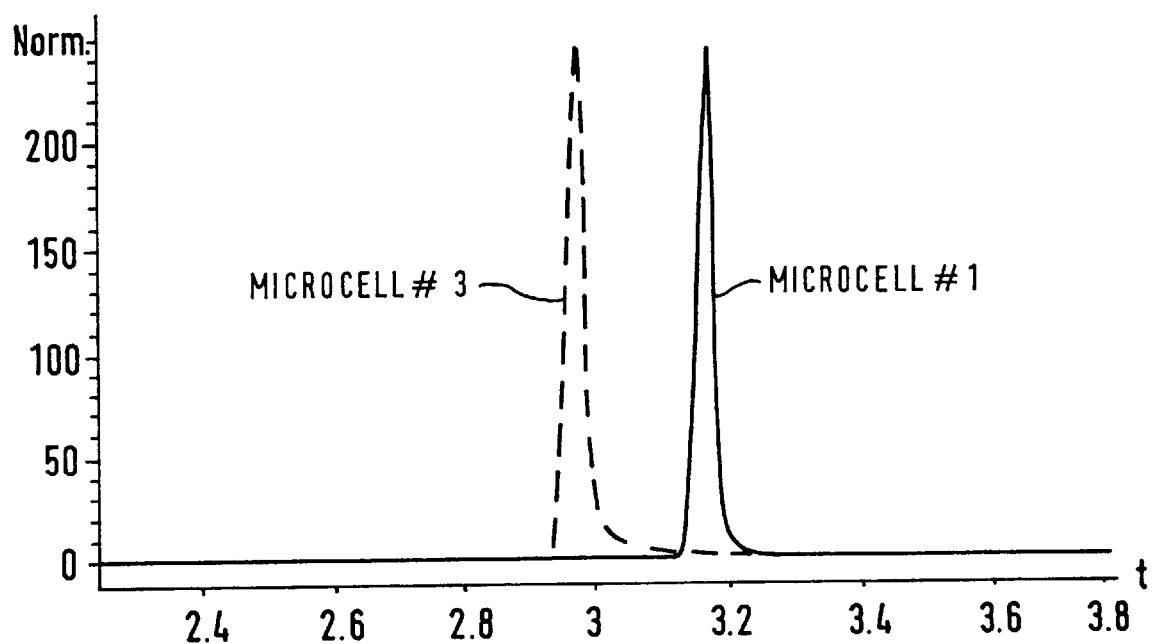
FIG. 6 is an electropherogram of the bandbroadening effect due to different diameters of the capillary and channel at the junction.

FIG. 6. is an electropherogram where a capillary with (microcell #1) and one without (microcell #2) expanded ID at the capillary/flow channel junction was used.

The electropherogram was recorded under the following conditions:

Buffer: Borate 20 mM pH8

Sample: p-hydroxyacetophenone (100 $\mu$M in water)

Cassette temperature: 25° C.

Injection: 100 mbarsec

Detection: 325 nm, 4 nm BW, 0,2 sec Rt.

Voltage: 25 kV

Capillary length: 56 cm

It can be clearly seen that the capillary having the straight end shows more peak tailing and thus lower efficiency.

Figure 7:
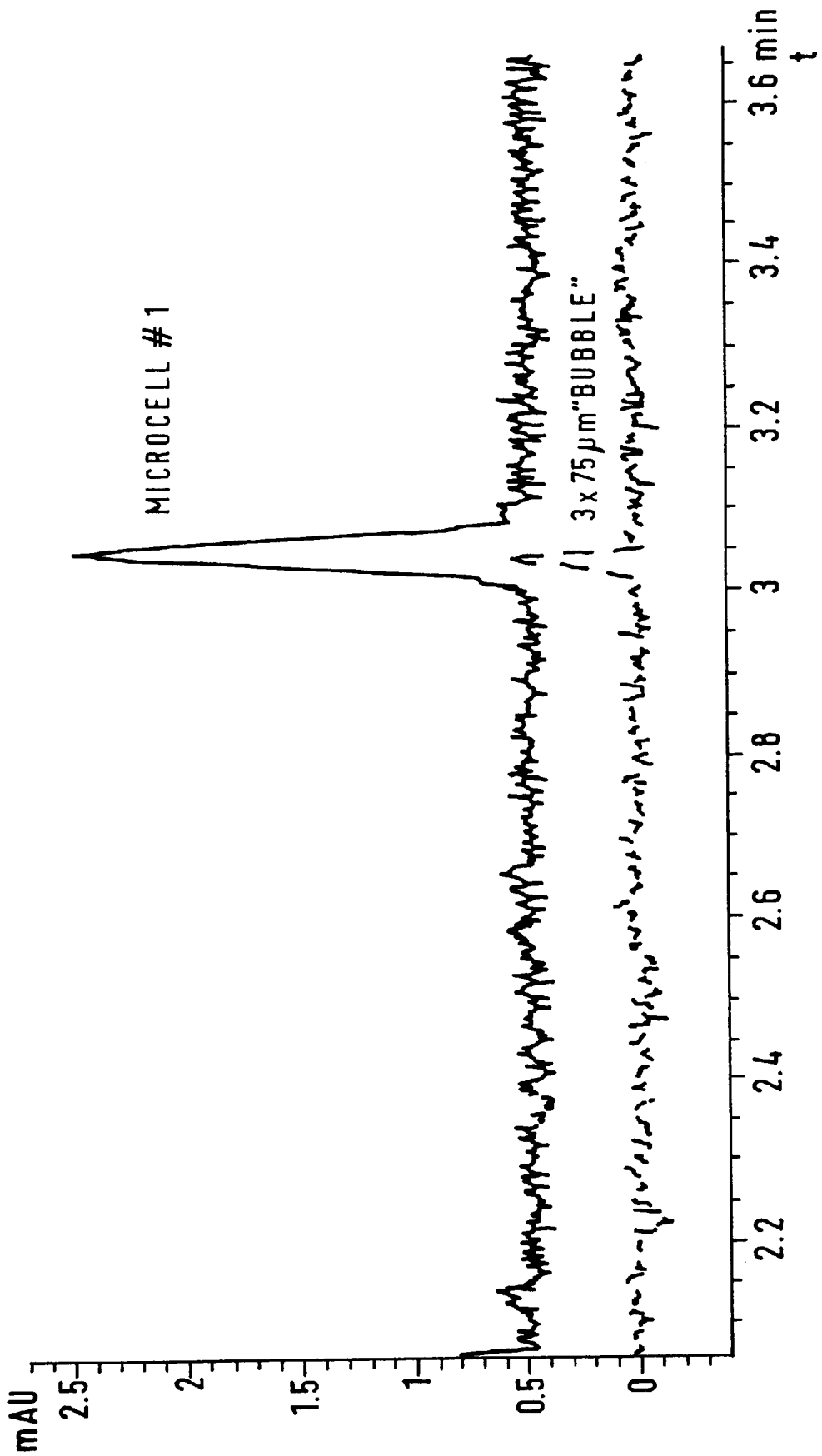
FIG. 7 is an electropherogram of the gain in sensitivity achieved by the present invention.
Figure 9:
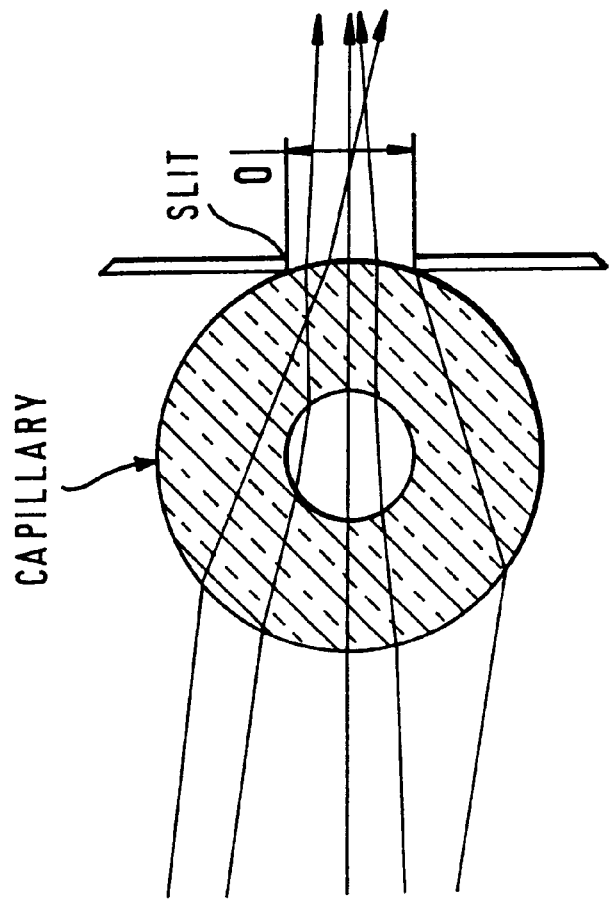
FIGS. 8 and 9 are respectively drawings of slit and capillary arrangements used in an on column approach.
Figure 8:
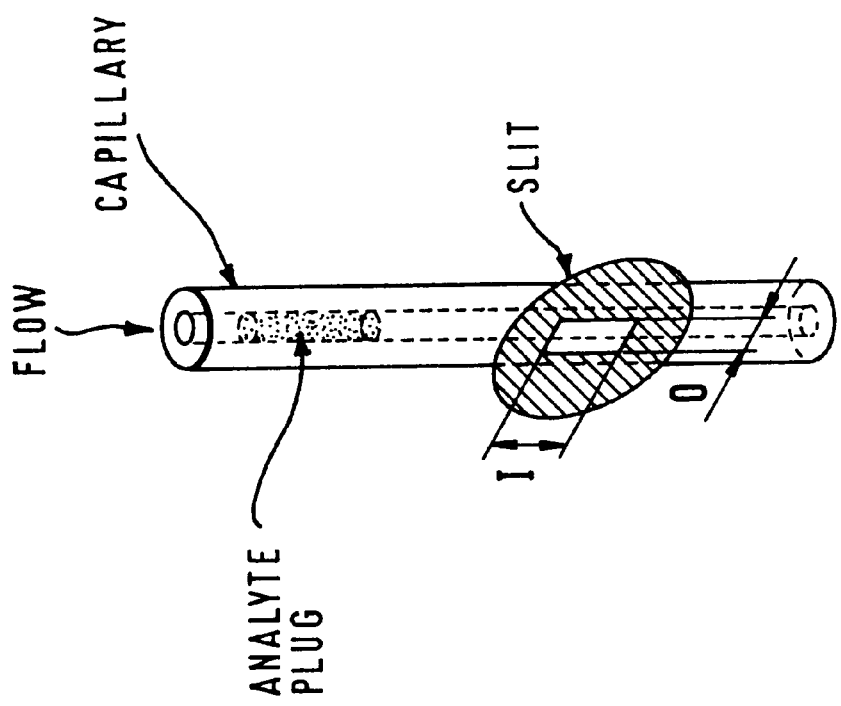
Figure 10:
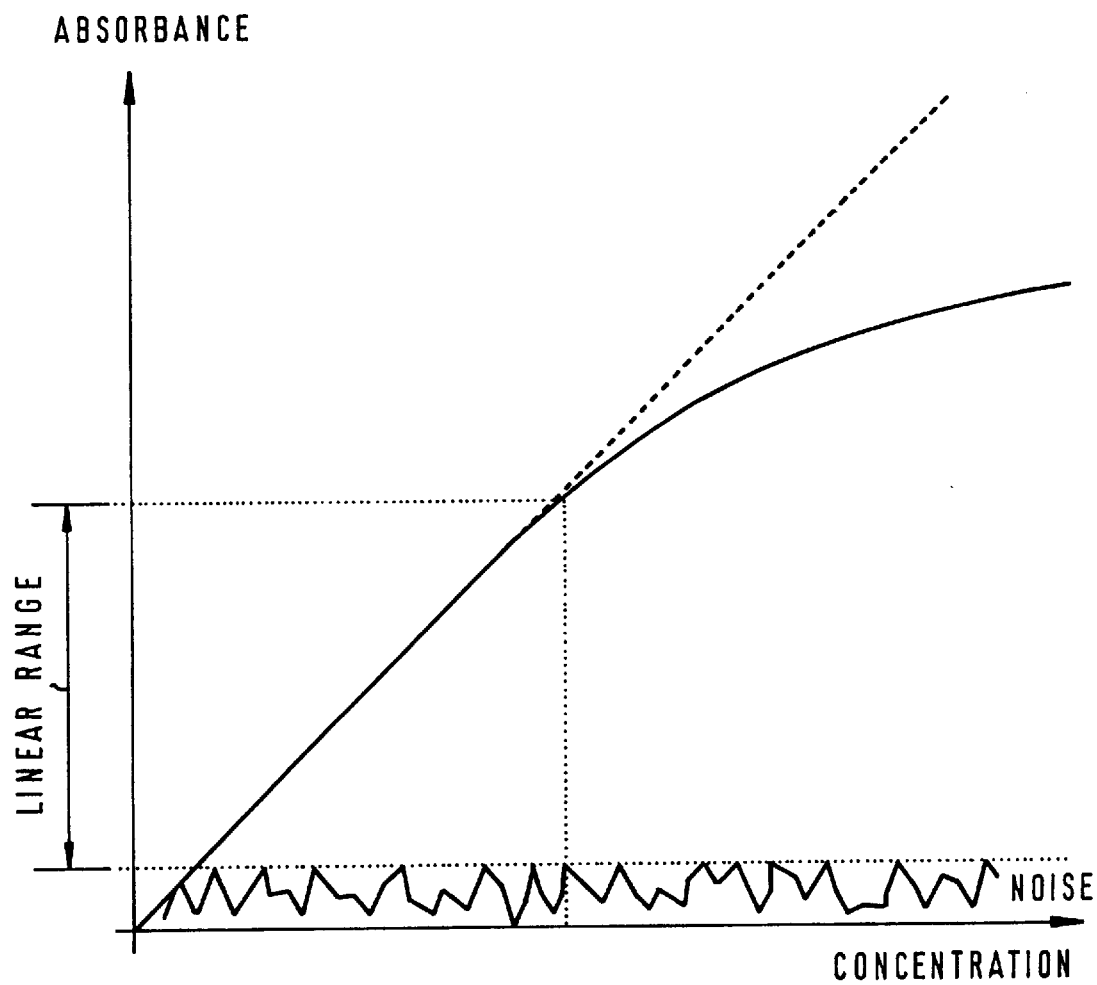
FIG. 10 is a graph of the principle detector response characteristic.
Figure 11:
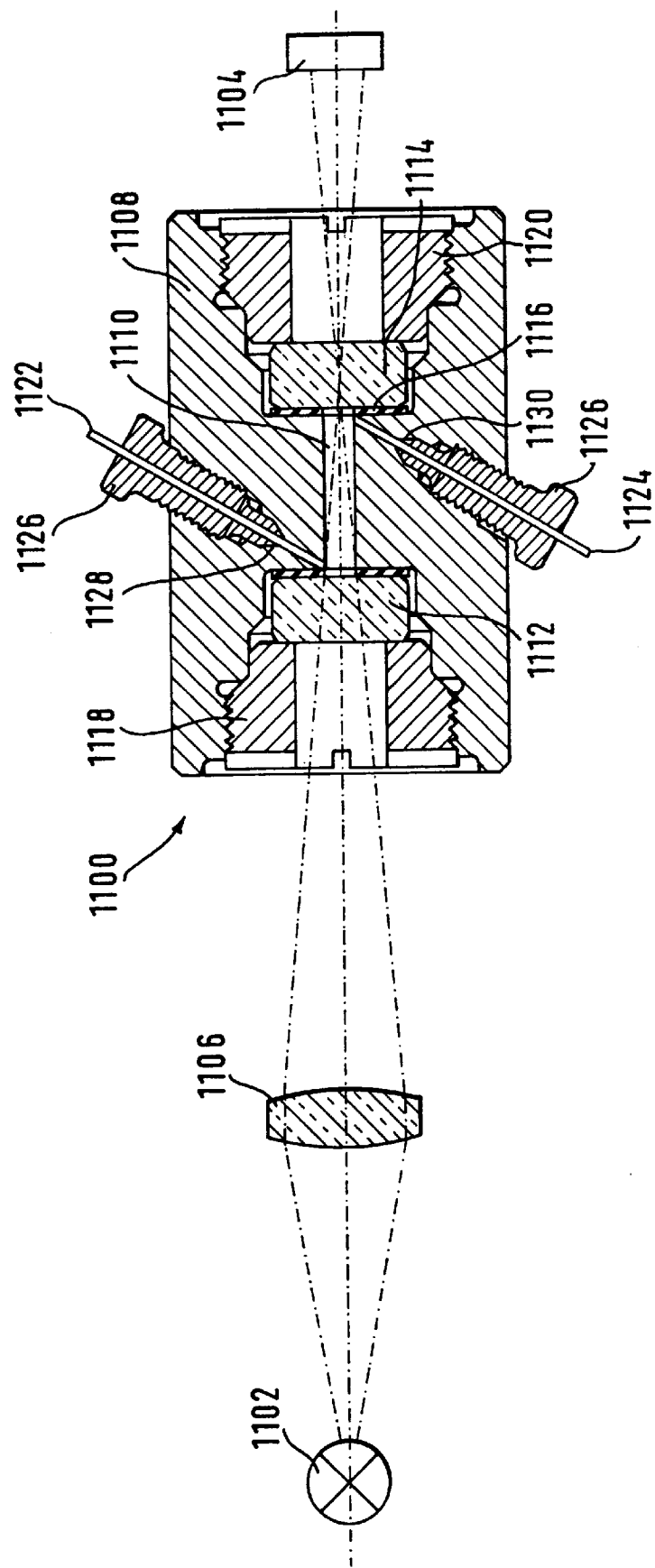
FIG. 11 is a diagram of a prior art flow cell used in liquid chromatography.

In FIG. 7 a graph is shown illustrating the gain in sensitivity readily achieved in an electrophoretic separation using a microcell according to the present invention.

The electropherogram was recorded under the following conditions:

Buffer: Borate 20 mM pH8

Sample: p-hydroxyacetophenone (1 $\mu$M in water)

Cassette temperature: 25° C.

Injection: 200 mbarsec, postinj. 100 mbarsec

Detection: 325 nm, 4 nm BW, 0,2 sec Rt.

Voltage: 25 kV

Capillary length: 56 cm

The cell according to the present invention was compared to the most sensitive on column detection approach that is readily available for capillary electrophoresis, using a capillary with 75 $\mu$m ID that is expanded three times at the point of detection.

The present invention offers unprecedented sensitivity in detection for liquid phase analysis of microscopic samples.

It has to be noted that the present invention is not limited to the transparent windows as described in the first and in the second embodiment or to the light input and light output waveguides. Other means for inputting the light into the flow cell and for outputting the light from the flow cell to a detector means can be used.

Although the present invention has been described in detail with reference to a particular preferred embodiment, persons processing ordinary skill in the art to which this invention pertains will appreciate that various modifications and enhancements may be made without departing from the spirit and scope of the claims that follow.

I claim:

1. Photometric apparatus for small sample volumes comprising:
    a cell body;
    a light input means arranged adjacent a first surface of the cell body;
    a light source for emitting light of predetermined wavelength or wavelength range through the light input means;
    a light output means arranged adjacent a second surface of the cell body opposite to the first surface;
    a light detector arranged adjacent the light output means; and
    a flow channel formed in the cell body; wherein surfaces of the walls of the channel have a roughness smaller than the predetermined wavelength or all wavelengths of the wavelength range of the source.

2. Apparatus according to claim 1, wherein the light input means comprises an optical input waveguide; and wherein the light output means comprises an optical output waveguide.

3. Apparatus according to claim 1, wherein the light input means comprises a first transparent window; and wherein the light output means comprises a second transparent window.

4. Apparatus according to claim 1, wherein the cell body is formed of non-transparent material.

5. Apparatus according to claim 3, wherein the flow channel comprises:
    a first portion formed adjacent to the first transparent window and extending substantially parallel to the first surface of the cell body;
    a second portion extending from the first surface to the second surface of the cell body; and
    a third portion formed adjacent to the second transparent window and extending substantially parallel to the second surface of the cell body.

6. Apparatus according to claim 1, comprising an inlet capillary and an outlet capillary in fluid connection with the flow channel.

7. Apparatus according to claim 1, wherein at least one of an inlet capillary and an output capillary has an expanded inner diameter at the capillary/flow channel junction.

8. Apparatus according to claim 6, comprising capillary support structure attached to the cell body for supporting the inlet and the outlet capillary.

9. Apparatus according to claim 8, wherein the inlet capillary and the outlet capillary are secured to the capillary support structure by glue or plastic fittings.

10. Apparatus according to claim 1, wherein the cell body comprises a first and a second portion, a first and a second flow channel forming part arranged between the first portion and the second portion of the cell body, wherein the cell body is formed by directly fusing together the first portion of the cell body, the first and second flow channels respectively forming parts, and the second portion.

11. Apparatus according to claim 4, wherein the flow channel includes junction portions connecting the flow channel portions under an angle of 45°.

12. Apparatus according to claim 1, wherein the flow channel has a rectangular cross-section of less than 150×150 $\mu$m and a channel length of less than 1.5 mm.

13. Apparatus according to claim 1, wherein the flow channel has a rectangular cross-section of less than 150×150 $\mu$m, a channel length of less than 1.5 mm and a total volume of less than 10 nl.

14. Apparatus according to claim 3, wherein the transparent windows are made of fused silica.

15. The photometric apparatus of claim 1 wherein the channel includes separate individual parts that are polished before being assembled to achieve the stated roughness.

16. A method of making a flow cell for use in liquid chromatography, the cell in use being responsive to optical energy having a predetermined wavelength or wavelength range, comprising determining the wavelength or wavelength range, forming in the cell an elongated flow channel for the liquid, the flow channel being arranged so in use of the cell the optical energy propagates and the liquid flows along the flow channel longitudinal axis, and machining and polishing the channel wall so the wall surface roughness has a value less than the determined wavelength or all wavelengths of the wavelength range of the source.

17. The method of claim 16, further including forming the channel from separate individual parts that are polished to achieve the stated channel wall surface roughness, the individual parts being polished to achieve the stated roughness prior to being assembled to form the channel.

18. Apparatus for use in spectroscopy analysis of small samples in liquid solution comprising a source of optical radiation having a predetermined wavelength or range of wavelengths, radiation from the source being directed in a predetermined direction, an optical detector for radiation from the source, a photometric flow cell including first and second members forming a cell body, the cell body including a flow channel for the liquid, the flow channel including a first component extending in the predetermined direction, the first component of the flow channel being defined by a slit between opposed edges of first and second plates bonded to the cell body and opposed faces of the first and second members, the edges of the plates and the opposed faces defining the first component of the flow channel having a roughness smaller than the predetermined wavelength or all wavelengths of the wavelength range of the source, first and second windows transparent to optical radiation from the source bonded to the cell body so that optical radiation from the source propagates through the first window, thence through the slit, thence through the second window and thence to the optical detector, the channel including second and third components connected to opposite sides of the slit for respectively supplying the liquid solution to the slit and removing the liquid solution from the slit.

19. Apparatus according to claim 18, wherein the second channel component includes a first passage between the first plate and the first window and the third channel component includes a second passage between the second plate and the second window.

20. Apparatus according to claim 18, wherein the slit has only planar faces.

21. Apparatus according to claim 18, wherein the slit has a cross-sectional area no greater than 0.25 square millimeters.

22. Apparatus according to claim 18, wherein the cell body and the plates are opaque to optical radiation of the source.

23. A method of making a photometric flow cell for use in spectroscopy analysis of small samples in liquid solution, the spectroscopy analysis being performed with an optical radiation source having a predetermined wavelength or range of wavelengths, the cell including first and second members having planar faces and a slit forming a component of a flow channel for the liquid sample, the method comprising polishing first and second edges of first and second plates so the edges have a roughness less than the predetermined wavelength or all wavelengths of the wavelength range of the source, then bonding faces of the plates to planar faces of the first and second members to form the slit of the flow channel for the liquid solution, then bonding windows transparent to the optical radiation to opposite faces of the members substantially at right angles to the flow direction of the liquid solution through the slit.

24. A method according to claim 23, wherein the plates are bonded to the members so there is (a) a first set back of another edge of the first plate from a face of the first window and a second set back of a further edge of the second plate from a face of the second window, and (b) the another and further edges are substantially transverse to the flow direction of the liquid solution through the slit, and (c) a first passage in the flow channel is formed between the another edge and the first window and a second passage in the flow channel is formed between the further edge and the second window.

* * * * *